United States Patent [19]

Henrick

[11] Patent Number: 4,661,617

[45] Date of Patent: Apr. 28, 1987

[54] NOVEL COMPOSITIONS

[75] Inventor: Clive A. Henrick, Palo Alto, Calif.

[73] Assignee: Sandoz Ltd., Basel, Switzerland

[21] Appl. No.: 725,453

[22] Filed: Apr. 19, 1985

[51] Int. Cl.[4] .............................................. C07C 69/76
[52] U.S. Cl. ............................................. 560/61; 560/9; 560/17; 568/308; 568/20; 568/43; 71/108; 71/123
[58] Field of Search ..................... 560/60, 61, 62, 63; 562/471; 514/543

[56] References Cited

U.S. PATENT DOCUMENTS

| | | | |
|---|---|---|---|
| 3,249,632 | 5/1966 | Peterson et al. | 560/61 |
| 3,452,081 | 6/1969 | Sprague et al. | 560/62 |
| 3,553,252 | 1/1971 | Mine et al. | 560/61 |
| 3,586,709 | 6/1971 | Richter et al. | 560/61 |
| 3,907,792 | 9/1975 | Mieville | 560/61 |
| 4,069,344 | 1/1978 | Karrer | 560/62 |
| 4,267,317 | 5/1981 | Koike et al. | 560/61 |
| 4,441,913 | 4/1984 | Aya et al. | 560/61 |

FOREIGN PATENT DOCUMENTS

| | | | |
|---|---|---|---|
| 53-130178 | 11/1978 | Japan | 514/543 |
| 56-34646 | 4/1981 | Japan | 560/61 |
| 56-53637 | 5/1981 | Japan | 560/62 |
| 2035317 | 6/1980 | United Kingdom | 560/62 |

OTHER PUBLICATIONS

Brooks et al., Pestic Sci., vol. 16(2), pp. 132–142 (1985).

*Primary Examiner*—James H. Reamer
*Attorney, Agent, or Firm*—Jacqueline S. Larson

[57] ABSTRACT

Substituted alkenoates and alkanoates, intermediates therefor, synthesis thereof, and their use for the control of pests.

3 Claims, No Drawings

NOVEL COMPOSITIONS

This invention relates to novel substituted alkenoates and related esters, intermediates therefor, synthesis thereof, and their use for the control of pests.

More particularly, the compounds of the present invention are represented by the following formula (A):

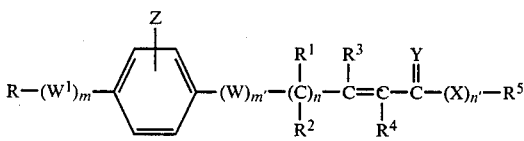

wherein,
each of m and m' is independently zero or one;
n is independently zero, one, two or three;
n' is zero or one;
R is hydrogen, lower alkyl, lower alkenyl, lower alkynyl, lower haloalkyl, lower haloalkenyl, lower haloalkynyl, lower alkoxyalkyl, lower alkylthioalkyl, halocycloalkyl, heterocycloalkyl or heterocycloalkylalkyl;
each of $R^1$, $R^2$, $R^3$, $R^4$, and $R^6$ is independently hydrogen or lower alkyl;
$R^5$ is hydrogen, lower alkyl, lower haloalkyl, lower alkenyl, lower alkynyl, lower haloalkenyl, lower haloalkynyl, lower alkoxyalkyl, lower alkylthioalkyl, cycloalkyl, cycloalkylalkyl, substituted or unsubstituted phenyl, pyridyl, furyl or thienyl;
W is oxygen, sulfur, $NR^6$ or carbonyl;
$W^1$ is oxygen, sulfur, sulfinyl, sulfonyl, $NR^6$ or carbonyl;
X is oxygen, sulfur or $NR^6$;
Y is oxygen or sulfur; and
Z is hydrogen, lower alkyl, lower haloalkyl, lower alkoxy or halogen.

In the description hereinafter and the claims, each of m, m' n, n', $R-R^6$, W, $W^1$, X, Y and Z is as defined above, unless otherwise specified.

The compounds of the present invention of formula (A) can be prepared by methods known in the art, such as those described in U.S. Pat. Nos. 3,824,274, 3,900,507 and 4,069,344 for example, and as outlined below:

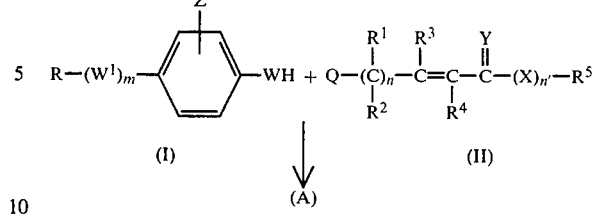

In the above synthesis, a phenol, benzenethiol or aniline of formula (I) is reacted with a halide of formula (II) (Q is chlorine, bromine or iodine) in an organic solvent such as N-methylpyrrolidone, dimethylformamide or tetrahydrofuran and at a reaction temperature of between 0° and 140°, preferably at between 10° and 110°, in the presence of a base such as potassium carbonate or sodium hydroxide. Alternatively, (when $R^5$ is not hydrogen) the salt of (I) is prepared with sodium hydride and this salt is reacted with a halide of formula (II).

Alternatively, (when $R^5$ is not hydrogen) a halide of formula (III) is reacted with an alcohol, thiol or amine (IV), following the above procedures.

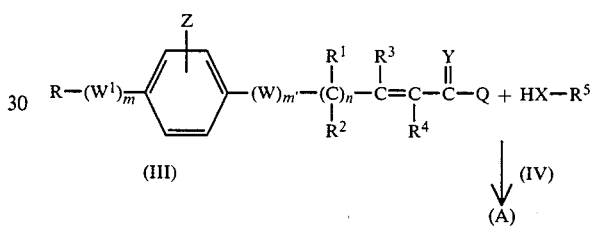

In a third synthetic method, a phenol, benzenethiol or aniline of formula (V) (when $R^5$ is not hydrogen) is reacted with sodium hydride to form the salt, and this salt is then reacted with a halide or methanesulfonate $R-Q^1$ (where $Q^1$ is halogen or mesyloxy), in an organic solvent at room temperature or above to give a compound of formula (A).

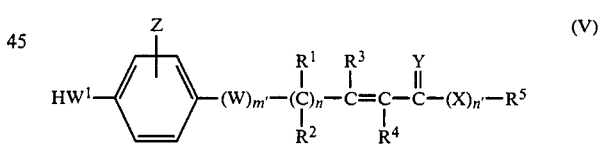

Compounds of formula (A) where m' is zero and $R^5$ is not hydrogen can be prepared by the Horner-Emmons-Wadsworth reaction of a ketone (VI), as follows:

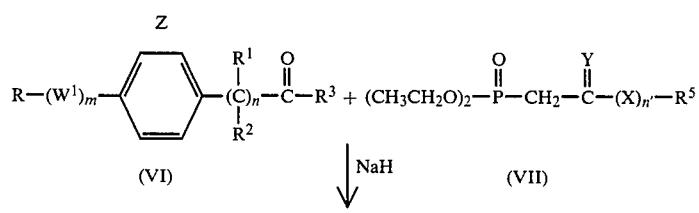

-continued

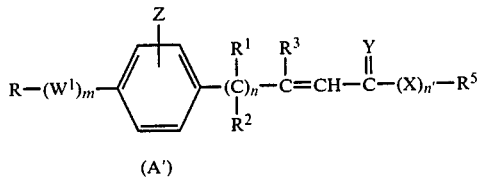

For example, in the above synthesis, a diethyl alkoxycarbonylmethylphosphonate (VII) and NaH are reacted together, and the resulting anion ester is reacted with a ketone (VI).

The starting materials of formulas (I) through (V) are known compounds, or they can be produced by methods analogous to known methods described in the literature.

Compounds of formula (A) where $W^1$ is sulfinyl are prepared by reacting a compound of formula (A) where $W^1$ is sulfur with one equivalent of sodium periodate or m-chloroperbenzoic acid in a solvent such as methanol or methylene chloride. Compounds where $W^1$ is sulfonyl are prepared in the same manner, except that two equivalents of m-chloroperbenzoic acid are used. Alternatively, either hydrogen peroxide in warm acetic acid or excess hydrogen peroxide with selenium dioxide is used as the oxidant.

Also included within the scope of the present invention are the corresponding alkanoates of the following formula (B):

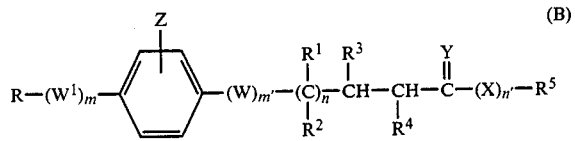

wherein the values for m, m', n, n', R–$R^6$, W, $W^1$, X, Y and Z are as defined above. The compounds of formula (B) are prepared by the hydrogenation of the corresponding alkenoates of formula (A), or by reduction of the alkenoates with sodium borohydride in the presence of $NiCl_2.6H_2O$ as described in *Chem. Parm. Bull.* 19:817 (1971).

The compounds of the present invention of formulas (A) and (B) can have one or more asymmetric centers and/or geometric isomers. The present invention includes each of the stereo isomers and the mixtures of stereo isomers thereof. In the examples hereinafter, unless otherwise specified, the compound is a mixture of stereo isomers.

The compounds of the present invention of formulas (A) and (B) are useful pest control agents, particularly for the control of insects, mites and ticks. The utility of these compounds as pest control agents is believed to be attributable to their juvenile hormone activity. They are preferably applied to the immature pest, namely during the embryo, larval or prepupal stage, in view of their effect on metamorphosis and otherwise abnormal development leading to death or inability to reproduce. These compounds can be effective control agents for insects of, for example, the orders Lepidoptera, Hemiptera, Homoptera, Coleoptera, Diptera, Orthoptera, and Siphonaptera, and other insects, and mites and ticks of the class Acara, including mites of the families Tetranychidae and Tarsonemidae and ticks of the families Argasidae and Ixodidae. The compounds can be applied to the pest or its locus in a pest controlling amount, usually of the order of 0.1 μg to 100 μg per insect, mite or tick.

In the use of the compounds of formulas (A) and (B) for combatting insects, a compound of formula (A) or (B), or mixtures thereof, can be combined with a carrier substance for application to the locus. The carrier can be liquid or solid and include adjuvants such as wetting agents. The compounds can be used in formulations such as wettable powders, solutions, dusts, granules, emulsifiable concentrates and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula (A) or (B) in the formulation can vary widely, generally within the range of 0.01 percent to 90.0 percent, by weight. Generally, a concentration of less than 25 percent of the active compound is employed.

The compounds of formula (A) and (B) can be combined with a cyclodextrin to make a cyclodextrin inclusion complex for application to the pest or its locus.

The compounds of the present invention can be used in combination with other pesticides such as the synthetic pyrethroids, carbamates, phosphates and insect growth regulators, or with insect attractants.

The following terms, wherever used in the description herein and in the appended claims, have the meaning defined below, unless otherwise specified hereinafter.

The term "lower alkyl" refers to an alkyl group, straight or branched, having a chain length of one to eight carbon atoms. The term "lower haloalkyl" refers to a lower alkyl group substituted with one to six halogen atoms.

The term "lower alkenyl" refers to an alkenyl group, straight or branched, having a chain length of two to eight carbon atoms and one or two ethylenic bonds. The term "lower haloalkenyl" refers to a lower alkenyl group substituted with one to six halogen atoms.

The term "lower alkynyl" refers to an alkynyl group, straight or branched, having a chain length of two to eight carbon atoms and one or two acetylenic bonds. The term "lower haloalkynyl" refers to a lower alkynyl group substituted with one to six halogen atoms.

The term "lower alkoxy" refers to an alkoxy group, straight or branched, having a chain length of one to eight carbon atoms.

The term "lower alkoxyalkyl" refers to an alkyl group substituted at one of the carbon atoms by an alkoxy group, straight or branched, the total number of carbon atoms being not greater than ten.

The term "lower alkylthioalkyl" refers to a lower alkyl group substituted at one of the carbon atoms by an alkylthio group, straight or branched, the total number of carbon atoms being not greater than ten.

The term "cycloalkyl" refers to a cycloalkyl group of three to eight cyclic carbon atoms. The term "cycloalkylalkyl" refers to a cycloalkyl group wherein one hydrogen atom is replaced by a lower alkyl group, the total number of carbon atoms being from four to twelve. The term "halocycloalkyl" refers to a cycloalkyl group substituted with one to six halogen atoms.

The term "heterocycloalkyl" refers to a heterocycloalkyl group, saturated or unsaturated, of two to six carbon atoms and one to three atoms selected from nitrogen, oxygen or sulfur. The term "heterocycloalkylalkyl" refers to a heterocycloalkyl group wherein one hydrogen is replaced by a lower alkyl group, the total number of carbon atoms being from three to twelve.

The term "substituted phenyl" refers to a phenyl group substituted at one, two or three of the ring carbon atoms with a group selected from lower alkyl, lower haloalkyl, lower alkoxy, lower haloalkoxy, halogen, nitro, cyano and lower alkylthio.

The following examples are provided to illustrate the practice of the present invention. Temperature is given in degrees Centigrade. RT stands for room temperature.

EXAMPLE 1

To ethyl 3-methyl-2-butenoate (10.0 g, 78.0 mmol) in 80 ml of carbon tetrachloride heated under gentle reflux is added N-bromosuccinimide (15.0 g, 84.0 mmol) in portions, followed by traces of radical initiator (benzoyl peroxide, ca. 0.2 g, and AIBN, ca. 0.1 g) in portions over one hour. After the final addition, the mixture is heated under reflux for 30 min. The reaction mixture is cooled and filtered and the solvent is removed by rotoevaporation to give ethyl 4-bromo-3-methyl-2-butenoate.

To 4-(1-methylpropoxy)phenol (0.84 g, 5.06 mmol) and potassium carbonate (0.66 g, 0.48 mmol) in 10 ml of dimethylformamide (DMF) at 5° is added ethyl 4-bromo-3-methyl-2-butenoate (1.0 g, 0.48 mmol). The mixture is allowed to warm to RT and is stirred at RT for 20 hours. The reaction mixture is poured into water and extracted with ether. The organic layer is washed with 10% sodium hydroxide to remove any starting phenol, dried and the solvent removed. The product is purified by preparative thin layer chromatography (prep. TLC). The second main band is collected to give ethyl (Z)-3-methyl-4-[4-(1-methylpropoxy)phenoxyl]-2-butenoate, MS m/e 292 (M+).

nmr (CDCl$_3$)δ2.02 (bs, 3H, (CH$_3$)C=C), centered at 4.18 (m, J=7Hz, 2H, OC$\underline{H}_2$CH$_3$), 5.14 (bs, 2H, ArOC$\underline{H}_2$), centered at 5.67 (m, 1H, vinyl proton) and 6.83 ppm (s, 4H, aromatic protons).

The third main band is collected to give ethyl (E)-3-methyl-4-[4-(1-methylpropoxy)phenoxy]-2-butenoate, MS m/e 292 (M+).

nmr (CDCl$_3$)δ2.20 (bs, 3H, (CH$_3$)C=C), centered at 4.19 (m, J=6.5Hz, 2H, OC$\underline{H}_2$CH$_3$), 4.47 (bs, 2H, ArOC$\underline{H}_2$), centered at 6.07 (m, 1H, vinyl proton), and 6.83 ppm (s, 4H, aromatic protons).

EXAMPLE 2

To sodium hydride (0.29 g, 12.0 mmol) in 20 ml of DMF is added 4-(1-methylpropoxy)phenol (2.0 g, 12.0 mmol) in 2 ml of DMF, maintaining the reaction temperature at 15°-25°. The mixture is stirred at RT for 1.5 hours, after which it is cooled to −25° and ethyl 4-bromo-3-methyl-2-butenoate (2.73 g, 13.2 mmol) is slowly added. The mixture is allowed to warm slowly to RT and is held at RT overnight. The reaction mixture is poured into water and extracted with ether, and the combined organic layers are washed with 10% sodium hydroxide and with water, dried and the solvent removed to give, after purification by prep. TLC, ethyl 3-methyl-4-[4-(1-methylpropoxy)phenoxy]-3-butenoate, MS m/e 292 (M+), as a mixture of isomers.

nmr (CDCl$_3$)δ centered at 1.73 (d, J=1.5Hz, 3H, Z isomer vinyl methyl), centered at 1.79 (d, J=1.5Hz, 3H, E isomer vinyl methyl), 2.98 (s, 2H, E isomer vinyl methylene), 3.23 (s, 2H, Z isomer vinyl methylene), 6.31 (m, 1H, vinyl proton) and 6.88 ppm (s, 4H, aromatic protons).

EXAMPLE 3

Following the procedure of Example 1, ethyl 4-bromo-3-methyl-2-butenoate is reacted with each of the alcohols under column I to give the corresponding butenoate under column II.

I 1. 4-(3-methyl-2-butenoxy)phenol
2. 4-(1-methylbutoxy)phenol
3. 4-(3-methoxy-3-methylbutoxy)phenol
4. 4-(3-chloro-2-propenoxy)phenol
5. 4-(1-methylpropylthio)phenol
6. 4-(1-methylpropylthio)phenylthiol
7. 2-fluoro-4-(1-methylpropoxy)phenol
8. 3-chloro-4-(1-methylpropoxy)phenol
9. 3-methyl-4-(1-methylpropoxy)phenol
10. 4-(1-methylpropoxy)-5-trifluoromethylphenol

II 1. ethyl 3-methyl-4-[4-(3-methyl-2-butenoxy)phenoxy]-2-butenoate
2. ethyl 3-methyl-4-[4-(1-methylbutoxy)phenoxy]-2-butenoate
3. ethyl 3-methyl-4-[4-(1-methoxy-3-methylbutoxy)phenoxy]-2-butenoate
4. ethyl 3-methyl-4-[4-(3-chloro-2-propenoxy)phenoxy]-2-butenoate
5. ethyl 3-methyl-4-[4-(1-methylpropylthio)phenoxy]-2-butenoate
6. ethyl 3-methyl-4-[4-(1-methylpropylthio)phenylthio]-2-butenoate
7. ethyl 3-methyl-4-[2-fluoro-4-(1-methylpropoxy)-phenoxy]-2-butenoate .
8. ethyl 3 methyl-4-]3-chloro-4-(1-methylpropoxy)-phenoxy]-2-butenoate
9. ethyl 3-methyl-4-[3-methyl-4-(1-methylpropoxy)-phenoxy]-2-butenoate
10. ethyl 3-methyl-4-[4-(1-methylpropoxy)-5-trifluoromethylphenoxy]-2-butenoate

EXAMPLE 4

Triethyl phosphonoacetate (16.55 g, 73.8 mmol) in 25 ml of DMF is added in portions to sodium hydride (1.04 g, 43.1 mmol), with ice bath cooling. The mixture is warmed to 35°. After 5.5 hours, the mixture is cooled to 20° and 4-[4-(1-methylpropoxy)phenyl]-2-butanone (2.71 g, 12.3 mmol) is added. After a further 4 hours at 20°, the reaction mixture is poured into ice and water and is extracted with ether. The combined organic layers are washed with 10% sodium hydroxide, with water and then with brine, dried and filtered, and the filtrate is concentrated in vacuo to give ethyl 3-methyl-5-[4-(1-methylpropoxy)phenyl]-2-pentenoate.

nmr (CDCl$_3$)δ0.96 (t, 3H, J=7.2Hz, CH(CH$_3$)CH$_2$CH$_3$), 1.85 (d, J=1Hz, vinyl CH$_3$, Z isomer), 2.19 (d, J=1Hz, vinyl CH$_3$, E isomer), centered at 4.13 (q, 2H, J=7.2Hz, OC$\underline{H}_2$CH$_3$), 5.60 (bs, 1H, vinyl H), centered at 6.79 (m, 2H, J=8.4Hz, aromatic protons), and centered at 7.05 ppm (m, 2H, J=8.4Hz, aromatic protons).

In the same way, triethyl phosphonoacetate is reacted with each of the ketones under column III to give the corresponding pentenoate under column IV.

III 11. 4-[4-(3-methyl-2-butenoxy)phenyl]-2-butanone
12. 4-[4-(3-methoxy-3-methylbutoxy)phenyl]-2-butanone
13. 4-[4-(1-methylpropylthio)phenyl]-2-butanone
14. 4-[4-(3-chloro-2-propenoxy)phenyl]-2-butanone

IV 11. ethyl 3-methyl-5-[4-(3-methyl-2-butenoxy)phenyl]2-pentenoate
12. ethyl 3-methyl-5-[4-(3-methoxy-3-methylbutoxy)phenyl]-2-pentenoate
13. ethyl 3-methyl-5-[4-(1-methylpropylthio)phenyl]2-pentenoate
14. ethyl 3-methyl-5-[4-(3-chloro-2-propenoxy)phenyl]-2-pentenoate

EXAMPLE 5

Vanillin (3.43 g, 22.5 mmol) in 10 ml of DMF is added portionwise, at 0°, to sodium hydride (21.5 g, 23.6 mmol) in ml of DMF. The mixture is stirred for 10 min. and then ethyl 4-bromo-3-methyl-2-butenoate (4.87 g, 23.5 mmol) in 3 ml of DMF is added. After 3 hours, the reaction mixture is poured into ether and 5% sodium hydroxide solution. The aqueous layer is extracted with ether, and the organic layers are combined and washed with 5% sodium hydroxide, with water and with brine and dried. Solvent is removed in vacuo and the crude product is chromatographed to give ethyl 3-methyl-4-(4-formyl-2-methoxyphenoxy)-2-butenoate. To isopropyltriphenylphosphonium iodide (2.26 g, 5.23 mmol) in 15 ml of tetrahydrofuran (THF) is added n-butyllithium (1.6 M; 3.10 ml, 5.0 mmol) at −5°. The mixture is cooled to −60°, and ethyl 3-methyl-4-(4-formyl-2-methoxyphenoxy)-2-butenoate (0.70 g, 2.51 mmol) in 10 ml of THF is added. After 45 min. the reaction mixture is poured into ether and water, and the aqueous phase is extracted with ether. The combined ether layers are washed with water and with brine and dried. Solvent is removed in vacuo, and the crude product is triturated with hexane and the hexane-soluble fraction is purified by prep. TLC to give ethyl 3-methyl-4-[2-methoxy-4-(2-methyl-1-propenyl)phenoxy]-2-butenoate, MS m/e 304 (M+).

nmr (CDCl$_3$)δ1.25 (t, J=7Hz, 3H), 1.85 (s, 6H), 2.02 (s, 3H), 3.84 (s, 3H), 4.14 (q, J=7Hz, 2H), 5.26 (s, 2H), 5 80 (bs, 1H), 6.19 (bs, 1H) and 6.53–6.97 ppm (3H, aromatic protons).

Following the above procedures, isobutyltriphenylphosphonium bromide (9.60 g, 24.0 mmol), n-butyllithium (9.0 mmol) and ethyl 3-methyl-4-(4-formyl-2-methoxyphenoxy)-2butenoate (1.67 g, 6.0 mmol) are reacted together to give ethyl 3-methyl-4-[2-methoxy-4-(3-methyl-1-butenyl)phenoxy]2-butenoate, MS m/e 318 (M+).

nmr (CDCl$_3$)δ0.83–1.43 (complex, 9H), 1.25 (t, J=Hz), 2.18 (s, 3H), 3.86 (s, 3H), 4.12 (q, J=7Hz, 2H), 4.53 (bs, 2H) and 6.63–6.97 ppm (3H, aromatic protons).

EXAMPLE 6

A mixture (2.90 g, 10.0 mmol) of ethyl 3-methyl-5-[4-(1-methylpropoxy)phenyl]-2-pentenoate and ethyl 3-methyl-5-[4-(1-methylpropoxy)phenyl]-3-pentenoate is combined with nickel chloride (129 mg, 1.0 mmol) and 80 ml of methanol and heated to 50°. Water (10 drops) is added to dissolve the nickel chloride. A second portion of nickel chloride (129 mg, 1.0 mmol) is heated with 10 drops of water, and the resulting solution is added, with 2 ml of methanol, to the mixture. The mixture is chilled to 15°, and sodium borohydride (757 mg, 20.0 mmol) is added in portions over 10 min. The mixture is allowed to warm to RT, and after 3.5 hours the nickel is removed by filtration. The filtrate is washed with methanol and concentrated in vacuo and water and ether are added. The aqueous phase is extracted with ether and the combined organic phases are washed with brine, dried, filtered and the filtrate concentrated to give ethyl 3-methyl-5-[4-(1-methylpropoxy)phenyl]-pentanoate.

nmr (CDCl$_3$)δcentered at 1.09 (m, 12H, 4X methyl groups), centered at 4.11 (m, 2H, OCH$_2$CH$_3$), centered at 6.78 (m, 2H, J=8.5Hz, aromatic protons), and centered at 7.06 ppm (m, 2H, J=8.5Hz, aromatic protons).

EXAMPLE 7

A mixture of platinum dioxide (50 mg) and sodium nitrite (3 mg) in 10 ml of 95% methanol/water is allowed to sit at RT for 10 min. under an atmosphere of hydrogen at NTP, after which ethyl 3-methyl-4-[4-(1-methylpropoxy)phenoxy]-2butenoate (1.30 g, 4.45 mmol) in 5 ml of 95% methanol/water is added by syringe with vigorous stirring. After ca. 2 hours, ca. 90 ml of H$_2$ had been taken up; the solvent is rotoevaporated off and ether is added to the reaction mixture. The organic phase is washed with water and with brine, dried and filtered and the filtrate is rotoevaporated to give, after purification by prep. TLC, ethyl 3-methyl-4[4-(1-methylpropoxy)phenoxy]butanoate, MS m/e 294 (M+).

nmr (CDCl$_3$)δcentered at 1.13 (m, 12H, methyl protons), centered at 3.81 (m, J=5.5Hz, 2H, Ar—O—CH$_2$), centered at 4.17 (q, J=6.5Hz, 2H, OCH$_2$CH$_3$) and 6.82 ppm (s, 4H, aromatic protons).

Following the above procedure, each of the butenoates under column II is hydrogenated to the corresponding butanoate.

EXAMPLE 8

Following the procedure of Example 1, each of methyl 4-bromo-3-methyl-2-butenoate, isopropyl 4-bromo-3-methyl-2-butenoate and n-propyl-4-bromo-3-methyl-2-butenoate is prepared and is then reacted with 4-(1-methylpropoxy)phenol to give, respectively, methyl 3-methyl-4-[4-(1-methylpropoxy)phenoxy]-2-butenoate
isopropyl 3-methyl-4-[4-(1-methylpropoxy)phenoxy]-2-butenoate
n-propyl 3-methyl-4-[4-(1-methylpropoxy)phenoxy]-2-butenoate.

Each of the above phenoxybutenoates is hydrogenated, following the procedure of Example 7, to give the corresponding phenoxybutanoate.

What is claimed is:
1. A compound of the following formula:

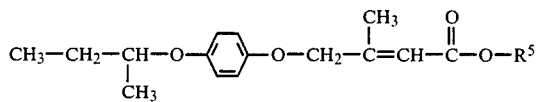
wherein, $R^5$ is $C_{1-8}$ alkyl, $C_{1-8}$ haloalkyl, $C_{2-8}$ alkenyl, $C_{2-8}$ alkynyl, $C_{2-8}$ haloalkenyl, $C_{2-8}$ haloalkynyl, $C_{2-10}$ alkoxyalkyl or $C_{2-10}$ alkylthioalkyl.
2. A compound according to claim 1 wherein $R^5$ is methyl or ethyl.
3. The compound ethyl 3-methyl-4-[4-(1-methylpropoxy)phenoxy]-2-butenoate, according to claim 2.
* * * * *